(12) United States Patent
Patt

(10) Patent No.: US 7,128,923 B2
(45) Date of Patent: *Oct. 31, 2006

(54) PRESERVED AND STABLE COMPOSITIONS CONTAINING PEPTIDE COPPER COMPLEXES AND METHOD RELATED THERETO

(75) Inventor: Leonard M Patt, Seattle, WA (US)

(73) Assignee: ProCyte Corporation, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/405,111

(22) Filed: Mar. 31, 2003

(65) Prior Publication Data

US 2004/0198639 A1    Oct. 7, 2004

(51) Int. Cl.
*A61K 8/64* (2006.01)
*A61K 38/02* (2006.01)
*A61K 38/08* (2006.01)

(52) U.S. Cl. .................. 424/400; 424/401; 424/450; 514/6; 514/18

(58) Field of Classification Search .......... 424/400, 424/401, 450, 484, 489, 630, 638; 514/2, 514/8, 18, 21; 530/300, 331, 343, 345
See application file for complete search history.

(56) References Cited

U.S. PATENT DOCUMENTS

| | | | |
|---|---|---|---|
| 4,665,054 A | 5/1987 | Pickart | 514/18 |
| 4,760,051 A | 7/1988 | Pickart | 514/6 |
| 4,767,753 A | 8/1988 | Pickart | 514/18 |
| 4,810,693 A | 3/1989 | Pickart | 514/18 |
| 4,877,770 A | 10/1989 | Pickart | 514/18 |
| 4,937,230 A * | 6/1990 | Pickart | 514/6 |
| 5,023,237 A | 6/1991 | Pickart | 514/18 |
| 5,059,588 A | 10/1991 | Pickart | 514/12 |
| 5,118,665 A | 6/1992 | Pickart | 514/6 |
| 5,120,831 A | 6/1992 | Pickart | 530/331 |
| 5,135,913 A | 8/1992 | Pickart | 514/16 |
| 5,164,367 A | 11/1992 | Pickart | 514/6 |
| 5,177,061 A | 1/1993 | Pickart | 514/18 |
| 5,214,032 A | 5/1993 | Pickart | 514/16 |
| 5,348,943 A | 9/1994 | Pickart | 514/18 |
| 5,538,945 A | 7/1996 | Pallenberg et al. | 514/6 |
| 5,550,183 A | 8/1996 | Pickart | 514/6 |
| 5,698,184 A * | 12/1997 | Pickart | 424/59 |
| 6,017,888 A | 1/2000 | Pallenberg et al. | 514/19 |
| 6,207,142 B1 * | 3/2001 | Odds et al. | 424/70.8 |
| 6,261,544 B1 * | 7/2001 | Coury et al. | 424/78.02 |
| 2003/0134781 A1 * | 7/2003 | Carmichael et al. | 514/6 |
| 2003/0206906 A1 * | 11/2003 | Semba | 424/145.1 |
| 2004/0076657 A1 * | 4/2004 | Wolfinbarger et al. | 424/423 |

FOREIGN PATENT DOCUMENTS

| | | |
|---|---|---|
| EP | 0 577 151 A1 * | 1/1994 |
| WO | WO 91/05797 | 5/1991 |
| WO | WO 91/07431 | 5/1991 |
| WO | WO 91/14437 | 10/1991 |
| WO | WO 95/35085 | 12/1995 |
| WO | WO 98/07438 | 2/1998 |
| WO | WO 03/030860 A1 | 4/2003 |
| WO | WO 03/030926 A1 | 4/2003 |
| WO | WO 03/047543 A1 | 6/2003 |
| WO | WO 2004/004671 A1 | 1/2004 |
| WO | WO 2004/014413 A1 | 2/2004 |
| WO | WO 2004/043481 A2 | 5/2004 |

OTHER PUBLICATIONS

Maquart et al., "In Vivo Stimulation of Connective Tissue Accumulation by the Tripeptide-Copper Complex Glycyl-$_L$-Histidyl-$_L$-Lysine-Cu$^{2+}$ in Rat Experimental Wounds," *J. Clin. Invest.* 92:2368-2376, Nov. 1993.

Maquart et al., "Stimulation of Collagen Synthesis in Fibroblast Cultures by the Tripeptide-Copper Complex Glycyl-$_L$-Histidyl-$_L$-Lysine-Cu$^{2+}$," *FEBS Letters* 238(2):343-346, Oct. 1988.

Wegrowski et al., "Stimulation of Sulfated Glycosaminoglycan Synthesis by the Tripeptide-Copper Complex Glycyl-$_L$-Histidyl-$_L$-Lysine-Cu$^{2+}$," *Life Sciences* 51(13):1049-1056, 1992.

\* cited by examiner

*Primary Examiner*—Jeffrey Edwin Russel
(74) *Attorney, Agent, or Firm*—Seed IP Law Group PLLC

(57) ABSTRACT

Compositions comprising at least one peptide copper complex and at least one preservative exhibit chemical stability of the peptide copper complex, as well as resistance and/or toxicity to microbial growth, when the preservative is selected to be a non-formaldehyde-donating preservative. In other embodiments, the present invention is directed to such compositions that are formulated for use as pharmaceuticals and cosmetic products, and to medical devices comprising a disclosed composition. In another aspect, the present invention is also directed to a method for imparting to a composition comprising at least one peptide copper complex, chemical stability as well as resistance and/or toxicity to microbial growth, where the method comprises incorporating a non-formaldehyde-donating preservative in the composition.

31 Claims, No Drawings

PRESERVED AND STABLE COMPOSITIONS CONTAINING PEPTIDE COPPER COMPLEXES AND METHOD RELATED THERETO

BACKGROUND OF THE INVENTION

1. Field of the Invention

The present invention generally relates to compositions comprising peptide copper complexes and, additionally, to such compositions formulated for use as pharmaceutical and cosmetic products, as well as to medical devices that comprise such compositions.

2. Description of the Related Art

Copper is known to have many beneficial biological applications, including, as a few examples, stimulating the accumulation of collagen and elastin, increasing the rate of wound healing, and increasing the amount of collagen in skin (see, e.g., Maquart, F. X., Pickart, L., Laurent, M., Gillery, P., Monboisse, J. C., Borel, J. P., "Stimulation of Collagen Synthesis in Fibroblast Cultures by the Tripeptide-Copper Complex Glycyl-L-Histidyl-L-Lysine-Copper(2+)," *FEBS Lett.* 238(2): 343–346, 1988; Wegrowski, Y., Maquart, F. X. and Borel, J. P., "Stimulation of Sulfated Glycosaminoglycan Synthesis by the Tripeptide-Copper Complex Glycyl-L-Histidyl-L-Lysine-Copper(2+)," *Life Sciences* 51: 1049–1056, 1992; Maguart, F. X., Bellon, G., Chaqour, B., Wegrowski, J., Patt L. M., Trachy, R. E., Monboisse, J. C., Chastang, F., Birembaut, P., Gillery, P. and Borel, J. P., "In Vivo Stimulation of Connective Tissue Accumulation by the Tripeptide-Copper Complex Glycyl-L-Histidyl-L-Lysine-Copper(2+) in Rat Experimental Wounds," *J. Clin. Invest.* 92: 2368–2376, 1993).

Copper salts alone are ineffective, or even inhibitory, for such applications. The copper must be delivered in a biologically acceptable form. As an example, when copper is complexed with a biologically acceptable carrier molecule, such as a peptide, it may then be effectively delivered to cells.

More specifically, peptide copper complexes, and compositions comprising the same, may be effective in this regard. Peptide copper complexes that are useful for wound healing and skin health are disclosed in U.S. Pat. Nos. 4,760,051; 4,665,054; 4,877,770; 5,135,913 and 5,348,943. Peptide copper complexes, beneficial for stimulating hair growth and preventing hair loss, are disclosed in U.S. Pat. Nos. 5,177,061; 5,214,032; 5,120,831; 5,550,183 and 5,538,945. Another beneficial application of peptide copper complexes is the prevention and healing of gastric ulcers, as disclosed in U.S. Pat. Nos. 5,145,838; 4,767,753 and 5,023,237. Yet another utility of such complexes is the healing of bone, as disclosed in U.S. Pat. No. 5,059,588.

While a number of compositions comprising peptide copper complexes have been identified and described as having biologically beneficial utility, there remains a need in the art for compositions that can more effectively, economically and readily be used for preparing pharmaceuticals, cosmetic products and medical devices. In particular, aqueous solutions of peptide copper complexes are needed that are suitable for storage at ambient conditions by virtue of being both chemically stable, and resistant and/or toxic to microbial growth. Also needed are pharmaceuticals, medical devices, or cosmetic products that comprise peptide copper complexes and which retain stability in the presence of preservatives used to resist microbial growth in such compositions. The present invention fulfills these needs and provides further related advantages.

BRIEF SUMMARY OF THE INVENTION

In brief, the present invention is directed to compositions comprising peptide copper complexes and having utility as pharmaceutical and cosmetic products, as well as medical devices, where the compositions are chemically stable, as well as resistant and/or toxic to microbial growth. The present invention is also directed to methods for preparing such compositions.

In one representative embodiment, the present invention provides a preserved and chemically stable composition comprising at least one peptide copper complex and at least one non-formaldehyde-donating preservative. It has been surprisingly found that a disclosed composition, by virtue of the selection and use of such a preservative, is both resistant and/or toxic to microbial growth and chemically stable with respect to the at least one peptide copper complex comprised therein.

In another representative embodiment, a composition is disclosed that comprises at least one peptide copper complex that is encapsulated in a liposome or microsponge adapted to aid in the delivery of the peptide copper complex or enhance the stability of the composition. In yet another representative embodiment, a composition is disclosed that comprises at least one peptide copper complex that is formulated in an instrument adapted to deliver the same via iontophoresis or ultrasound.

As previously noted, peptide copper complexes, and compositions comprising the same, have beneficial utility for, as some examples, skin health and appearance; wound healing; hair, bone and tissue growth; and hair loss prevention. Accordingly, the present invention, in another embodiment, is directed to a composition that further comprises an inert and physiologically acceptable carrier or diluent, thus being suitable for use as a pharmaceutical or cosmetic product. In a related embodiment, a medical device is disclosed that comprises a composition of the present invention.

The present invention, in another representative embodiment, is directed to a method for inhibiting microbial growth and/or reducing microbe populations in a composition comprising at least one peptide copper complex, while also substantially preserving the chemical stability of the at least one peptide copper complex. The method comprises incorporating a non-formaldehyde-donating preservative in the composition.

These and other aspects of the present invention will be evident upon reference to the following detailed description of the invention.

DETAILED DESCRIPTION OF THE INVENTION

As noted above, in one embodiment of the present invention, a preserved and chemically stable composition is disclosed that comprises at least one peptide copper complex and at least one non-formaldehyde-donating preservative. In related, more specific embodiments, the at least one peptide copper complex is glycyl-L-histidyl-L-lysine:copper(II) ("GHK-Cu"), L-alanyl-L-histidyl-L-lysine:copper(II) ("AHK-Cu") and L-valyl-L-histidyl-L-lysine:copper(II) ("VHK-Cu").

As used herein, the term "peptide copper complex" generally refers to a coordination compound comprising a peptide molecule and a copper(II) ion non-covalently complexed therewith. As is well understood in the art, copper (II) designates a copper ion having a valence of 2 (i.e., $Cu^{+2}$). The peptide molecule serves as the complexing agent by donating electrons to the copper ion to yield the non-covalent complex. The peptide molecule is a chain of two or more amino acid units or amino acid derivative units covalently bonded together via amide linkages, the formation of such linkages being accompanied by the elimination of water.

Generally, an amino acid consists of an amino group, a carboxyl group, a hydrogen atom, and an amino acid side-chain moiety—all bonded, in the case of an alpha-amino acid, to a single carbon atom that is referred to as an alpha-carbon. The amino acid units of the present invention may be provided by amino acids other than alpha-amino acids. For example, the amino acids may be beta- or gamma-amino acids, such as those shown below.

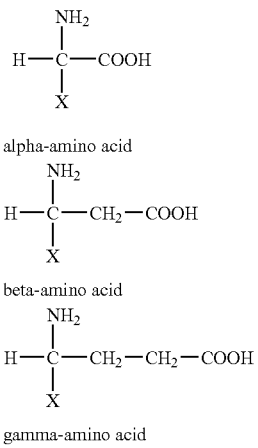

alpha-amino acid beta-amino acid gamma-amino acid where X is the amino acid side-chain moiety bonded, along with the amino group and hydrogen, to an alpha-, beta-, or gamma-carbon atom.

As another example, the amino acids include, but are not limited to, naturally occurring alpha-amino acids. Naturally occurring amino acids are those from which the amino acid units of naturally occurring proteins are derived. Some of these amino acids, along with their respective amino acid side chain moieties, are shown below in Table 1. The naturally occurring amino acids shown are all in the L configuration, referring to the optical orientation of the alpha carbon or other carbon atom bearing the amino acid side chain. A peptide molecule of the present invention may also comprise amino acids that are in the D optical configuration, or a mixture thereof.

TABLE 1

Naturally Occurring Amino Acid Side-Chain Moieties

| Amino Acid Side Chain Moiety | Amino Acid |
|---|---|
| —H | Glycine |
| —CH$_3$ | Alanine |
| CH(CH$_3$)$_2$ | Valine |

TABLE 1-continued

Naturally Occurring Amino Acid Side-Chain Moieties

| Amino Acid Side Chain Moiety | Amino Acid |
|---|---|
| CH$_2$CH(CH$_3$)$_2$ | Leucine |
| CH(CH$_3$)CH$_2$CH$_3$ | Isoleucine |
| —(CH$_2$)$_4$NH$_3$$^+$ | Lysine |
| —(CH$_2$)$_3$NHC(NH$_2$)NH$_2$$^+$ | Arginine |
| —CH$_2$-(imidazole) | Histidine |
| —CH$_2$COO— | Aspartic Acid |
| —CH$_2$CH$_2$COO— | Glutamic Acid |
| —CH$_2$CONH$_2$ | Asparagine |
| —CH$_2$CH$_2$CONH$_2$ | Glutamine |
| —CH$_2$-(phenyl) | Phenylalanine |
| —CH$_2$-(phenyl)-OH | Tyrosine |
| —CH$_2$-(indole) | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| (pyrrolidine ring) | Proline |

Other naturally occurring amino acids include hydroxyproline and gamma-carboxyglutamate.

Representative amino acid derivatives include those set forth in Table 2 below.

TABLE 2

Amino Acid Derivatives

NH—CH—COOH
    |    |
   X$_1$  X$_2$

Where $X_2$ = H or the following moieties:

—(CH$_2$)$_n$CH$_3$ where n = 1–20
—(CH$_2$)$_n$CH(CH$_3$)(CH$_2$)$_m$CH$_3$ where n, m = 0–20 (when n = 0, m ≠ 0 or 1 and when n = 1, m ≠ 0)
—(CH$_2$)$_n$NH$_2$ where n = 1–20 (n ≠ 4)
—(CH$_2$)$_n$CONH$_2$ where n = 3–20
—(CH$_2$)$_n$COOH where n = 3–20

—(CH$_2$)$_n$-(phenyl)-OH where n = 2–20

TABLE 2-continued

Amino Acid Derivatives $$\begin{array}{c} NH-CH-COOH \\ | \quad\quad | \\ X_1 \quad\; X_2 \end{array}$$

—(CH$_2$)$_n$—⟨phenyl⟩—OH where n = 2 = 2–20

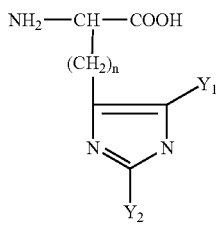

where n = 2–20

—(CH$_2$)SH where n = 2–20
—(CH$_2$)$_n$S(CH$_2$)$_m$CH$_3$ where n, m = 1–20 (when n = 2, m ≠ 0)
—(CH$_2$)$_n$CH$_2$OH where n = 1–20
—(CH$_2$)$_n$CH(CH$_3$)OH where n = 1–20
And where X$_1$ = H or the following moieties:

—(CH$_2$)$_n$CH$_3$ where n = 0–20
—(CH$_2$)$_n$CH(CH$_3$)(CH$_2$)$_m$CH$_3$ where n, m = 0–20

Histidine derivatives of this invention include compounds having the structure:

$$\begin{array}{c} NH_2-CH-COOH \\ | \\ (CH_2)_n \\ \diagdown \\ \text{imidazole with } Y_1, Y_2 \end{array}$$

where n=1–20, and Y$_1$ and Y$_2$ are independently selected from alkyl moieties containing from 1–12 carbon atoms or an aryl moiety containing from 6–12 carbon atoms. In certain embodiments, n is 1, Y$_2$ is methyl, and Y$_1$ is H (i.e., 3-methyl histidyl) or Y$_2$ is H and Y$_1$ is methyl (i.e., 5-methyl histidine).

As used herein, "alkyl" means a straight chain or branched, cyclic or noncyclic, substituted or unsubstituted, saturated or unsaturated aliphatic hydrocarbon containing from 1 to 18 carbon atoms. Representative saturated straight chain alkyls include methyl, ethyl, n-propyl and the like; while saturated branched alkyls include isopropyl, sec-butyl, isobutyl, tert-butyl, isopentyl, and the like. Representative, saturated cyclic alkyls include cyclopropyl, cyclobutyl, cyclopentyl, —CH$_2$cyclohexyl, and the like; while unsaturated cyclic alkyls include cyclopentenyl, cyclohexenyl, and the like. Unsaturated alkyls contain at least one double or triple bond between adjacent carbon atoms (referred to as an "alkenyl" or "alkynyl," respectively). Representative alkenyls include ethylenyl, 1-butenyl, isobutylenyl, 2-methyl-2-butenyl, and the like; while representative alkynyls include acetylenyl, 2-butynyl, 3-methyl-1-butynyl, and the like.

Also, as used herein, "aryl" means an aromatic carbocyclic moiety such as phenyl or naphthyl, and may be substituted or unsubstituted. "Arylalkyl," as used herein, means an alkyl having at least one alkyl hydrogen atom replaced with a substituted or unsubstituted aryl moiety, such as benzyl (i.e., —CH$_2$phenyl, —(CH$_2$)$_2$phenyl, —(CH$_2$)$_3$phenyl, —CH(phenyl)$_2$, and the like).

Similarly, arginine derivatives of this invention include compounds having the structure:

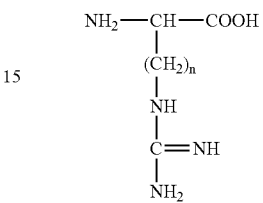

where n=1–20 (excluding n=3).

A peptide copper complex of the present invention may have the formula [R$_1$-R$_2$-R$_3$]:copper(II) where R$_3$ is at least one amino acid or amino acid derivative, as defined above, bonded to R$_2$ by a peptide bond (i.e., —C(=O)NH—). Where R$_3$ is a single amino acid or amino acid derivative, then the peptide of the peptide copper complex is generally classified as a tripeptide. As another example of a peptide copper complex of the present invention having the formula [R$_1$-R$_2$-R$_3$]:copper(II), R$_3$ is a chemical moiety bonded to the R$_2$ moiety by an amide bond. The expression "chemical moiety," as used herein and with reference to R$_3$, includes any chemical moiety having an amino group capable of forming an amide bond with the carboxyl terminus of R$_2$ (i.e., the carboxyl terminus of histidine, Arginine, or derivatives thereof).

As a more particular example, where R$_3$ is a chemical moiety bonded to the R$_2$ moiety by an amide bond, R$_3$ is —NH$_2$, an alkylamino moiety having from 1–20 carbon atoms, or an arylamino moiety having from 6–20 carbon atoms. As used herein, an "alkylamino moiety" encompasses alkyl moieties containing an amino moiety, wherein the alkyl moiety is as defined above, and includes, but is not limited to, octyl amine and propyl amine. Similarly, an "arylamino moiety" encompasses aryl moieties containing an amino moiety, wherein the aryl moiety is as defined above, and includes, but is not limited to, benzylamine and benzyl-(CH$_2$)$_{1-14}$-amine. Further examples of suitable chemical moieties having amino groups capable of forming an amide linkage with the carboxyl terminus of R$_2$ include polyamines such as spermine and sperimidine.

It should be understood that R$_3$ may include more than one chemical moiety. For example, additional amino acids or amino acid derivatives may be bonded to the above-described peptide copper complexes comprising tripeptides to yield peptide copper complexes comprising peptides having four or more amino acids and/or amino acid derivatives. For purposes of illustration, Table 3, shown below, presents various representative examples of peptide copper complexes of the present invention.

TABLE 3

Representative Peptide-Copper Complexes

Examples of [R₁-R₂]:copper(II)

| | |
|---|---|
| glycyl-histidine:copper | alanyl-histidine:copper |
| glycyl-(3-methyl)histidine:copper | alanyl-(3-methyl)histidine:copper |
| glycyl-(5-methyl)histidine:copper | alanyl-(5-methyl)histidine:copper |
| glycyl-arginine:copper | alanyl-arginine:copper |
| (N-methyl)glycine-histidine:copper | (N-methyl)glycine-arginine:copper |

Examples of [R₁-R₂-R₃]:copper(II) where R₃ is Chemical Moiety Linked by Amide Bond

| | |
|---|---|
| glycyl-histidyl-NH₂:copper | glycyl-arginyl-NH₂:copper |
| glycyl-(3-methyl)histidyl-NH₂:copper | alanyl-(3-methyl)histidyl-NH₂:copper |
| glycyl-arginyl-NH₂:copper | alanyl-arginyl-NH₂:copper |
| (N-methyl)glycine-histidyl-NH₂:copper | (N-methyl)glycine-arginyl-NH₂:copper |
| glycyl-histidyl-NHoctyl:copper | glycyl-arginyl-NHoctyl:copper |

Examples of [R₁-R₂-R₃]:copper(II) where R₃ is Amino Acid or Amino Acid Derivative Linked by Peptide Bond

| | |
|---|---|
| glycyl-histidyl-lysine:copper | glycyl-arginyl-lysine:copper |
| glycyl-(3-methyl)histidyl-lysine:copper | glycyl-(5-methyl)histidyl-lysine:copper |
| alanyl-histidyl-lysine:copper | alanyl-arginyl-lysine:copper |
| alanyl-(3-methyl)histidyl-lysine:copper | alanyl-(5-methyl)histidyl-lysine:copper |
| glycyl-histidyl-phenylalanine:copper | glycyl-arginyl-phenylalanine:copper |
| glycyl-(3-methyl)histidyl-phenylalanine:copper | glycyl-(5-methyl)histidyl-phenylalanine:copper |
| alanyl-histidyl-phenylalanine:copper | alanyl-arginyl-phenylalanine:copper |
| alanyl-(3-methyl)histidyl-phenylalanine:copper | alanyl-(5-methyl)histidyl-phenylalanine:copper |
| glycyl-histidyl-lysyl-phenylalanyl-phenylalanyl:copper | glycyl-arginyl-lysyl-phenylalanyl-phenylalanyl:copper |
| glycyl-(3-methyl)histidyl-lysyl-phenylalanyl-phenylalanyl:copper | glycyl-(5-methyl)histidyl-lysyl-phenylalanyl-phenylalanyl:copper |
| (N-methyl)glycyl-histidyl-lysine:copper | (N-methyl)glycyl-arginyl-lysine:copper |
| valyl-histidyl-lysine:copper | glycyl-histidyl-lysyl-prolyl-phenylalanyl-proline:copper |
| prolyl-histidyl-lysine:copper | |
| glycyl-D-histidyl-L-lysine:copper | Leucyl-histidyl-lysine:copper |
| seryl-histidyl-lysine:copper | |

Further examples of peptide copper complexes encompassed in embodiments of the present invention are disclosed in U.S. Pat. Nos. 4,665,054; 4,760,051; 4,767,753; 4,810,693; 4,877,770; 5,023,237; 5,059,588; 5,118,665; 5,120,831; 5,164,367; 5,177,061; 5,214,032; 5,538,945; 5,550,183; and 6,017,888, all of which are incorporated herein by reference in their entirety.

Examples of the peptide copper complex derivatives, encompassed in embodiments of the present invention, include, but are not limited to, those disclosed and described in the above-cited U.S. Patents that are directed to peptide copper complexes, as well as those disclosed and described in the published PCT application having the international publication number WO 94/03482, incorporated herein by reference in its entirety.

The synthesis of the above-disclosed peptide copper complexes is described in detail in the above-referenced patents. For example, the peptides of the peptide copper complexes disclosed herein may be synthesized by either solution or solid phase techniques known to one skilled in the art of peptide synthesis. The general procedure involves the stepwise addition of protected amino acids to build up the desired peptide sequence. The resulting peptide may then be complexed to copper (at the desired molar ratio of peptide to copper) by dissolving the peptide in water, followed by the addition of copper chloride or other suitable copper salt and adjusting the pH to greater than 4.0.

Aqueous solutions of peptide copper complexes are prepared by methods that are well known to one skilled in the art. For example, an amount of dried peptide copper complex, suitable for a desired concentration, is readily dissolved in water with mixing and gentle heating. An alternative method is to prepare a solution of the desired peptide, followed by the addition of a copper salt in the desired molar ratio to yield the desired solution of the peptide copper complex. Examples of copper salts that may be used are cupric chloride and cupric acetate. When aqueous solutions of peptide copper complexes are prepared, the solutions are neutralized, typically with NaOH.

In further, more specific embodiments of the disclosed preserved and chemically stable composition, the molar ratio of peptide to copper in the at least one peptide copper complex thereof ranges from 1:1 to 3:1; and the preserved and chemically stable composition is an aqueous solution having a pH ranging from about 4.5 to about 7.5. In yet further, more specific embodiments, the at least one peptide copper complex is present at a concentration ranging from about 0.05% to about 25%; from about 0.05% to about 2%; and from about 0.1% to about 0.5%, respectively.

In yet another embodiment of the present invention, the peptide portion of the peptide copper complex may also be of natural origin. In this embodiment, the peptide is formed by the hydrolysis of naturally occurring proteins, polypeptides, or larger peptides of either plant, microbial, or animal origin. Hydrolysis may be by enzymatic treatment or by acid or base hydrolysis to form a mixture of peptides. The copper complex of this type of peptide copper complex is formed by addition of a suitable copper salt to the aqueous solution of the peptide or peptide mixture. Alternatively, the peptide copper complex may be formed during the manufacturing of a formulation by separate additions of the peptide and copper salt in a suitable solvent.

As disclosed above, the preserved and chemically stable composition of the present invention comprises a non-formaldehyde-donating preservative, in addition to the at least one peptide copper complex. As used herein, the term "preservative" refers to a compound or mixture of compounds that inhibits microbial growth and/or reduces microbe populations in a composition, thereby protecting associated products from spoilage. Also, as used herein, the expression "non-formaldehyde-donating preservative" refers to such a preservative that does not decompose to release formaldehyde (i.e., does not derive its activity as a preservative from the release of formaldehyde).

In contrast, a formaldehyde-donating preservative, when added, for example, to an aqueous solution comprising a peptide copper complex, does decompose to release formaldehyde, which inhibits microbial growth. Examples of formaldehyde-donating preservatives include, but are not limited to, Diazolidinyl Urea, Imidazolidinyl Urea, and DMDM Hydantoin (1,3-Dimethylol-5,5-Dimethyl Hydantoin), Diethylol Dimethyl Hydantoin, Diethylol Dimethyl Hydantoin Dilaurate, and the like.

It has been discovered that peptide copper complexes exhibit increased rates of chemical breakdown in the presence of formaldehyde-donating preservatives. Thus, it has been discovered that, by selecting only non-formaldehyde-donating preservatives for combining with compositions comprising a peptide copper complex, microbial growth can be inhibited, or microbe populations reduced, in such compositions without causing the chemical breakdown of the peptide copper complex.

Representative examples of non-formaldehyde-donating preservatives that are suitable for use in the present invention, include, but are not limited to: Ammonium Benzoate, Ammonium Propionate, Benzisothiazolinone, Benzoic Acid, Benzotriazole, Benzyl Alcohol, Benzylparaben, 5-Bromo-5-Nitro-1,3-Dioxane, 2-Bromo-2-Nitropropane-1, 3-Diol, Butyl Benzoate, Butylparaben, Calcium Benzoate, Calcium Paraben, Calcium Propionate, Calcium Salicylate, Calcium Sorbate, Chlorhexidine Diacetate, Chlorhexidine Digluconate, Chlorhexidine Dihydrochloride, Chloroacetamide, Chlorobutanol, p-Chloro-m-Cresol, Chlorophene, p-Chlorophenol, Chlorophenesin, Chlorothymol, Chloroxylenol, m-Cresol, o-Cresol, p-Cresol, Dehydroacetic Acid, Dibromopropamidine Diisethionate, Dimethyl Oxazolidine, Dithiomethylbenzamide, Domiphen (N,N-Dimethyl-N-(2-Phenoxyethyl)-1-Dodecanaminium) Bromide, Ethyl Ferulate (Cinnamic Acid, 4-Hydroxy-3-Methoxy-, Ethyl Ester), Ethylparaben, Ferulic Acid (Cinnamic Acid, 4-Hydroxy-3-Methoxy-), Glyoxal, Hexamidine, Hexamidine Diparaben, Hexamidine Paraben, 4-Hydroxybenzoic Acid, Hydroxymethyl Dioxoazabicyclooctane, Iodopropynyl Butylcarbamate, Isobutylparaben, Isodecylparaben, Isopropyl Cresols, Isopropylparaben, Isopropyl Sorbate, Lauryl Diethylenediaminoglycine HCl, Magnesium Benzoate, Magnesium Propionate, MEA-Benzoate, MEA o-Phenylphenate, Methylchloroisothiazolinone, Methyl-dibromo Methylisothiazolinone, Methylparaben, Octylisothiazolinone, Panthenyl Ethyl Ether Benzoate, Phenethyl Alcohol, Phenol, Phenoxyethanol, Phenoxyethylparaben, Phenoxyisopropanol, Phenyl Benzoate, Phenylparaben, o-Phenylphenol, Polymethoxy Bicyclic Oxazolidine, Potassium Benzoate, Potassium Butylparaben, Potassium Ethylparaben, Potassium Methylparaben, Potassium Paraben, Potassium Phenoxide, Potassium o-Phenylphenate, Potassium Propionate, Potassium Propylparaben, Potassium Sorbate, Propionic Acid, Propyl Benzoate, Propylparaben, Quaternium-8 (Methyl and Stearyl Dimethylaminoethyl Methacrylate Quaternized with Dimethyl Sulfate), Quaternium-14 (Ethanaminium, N,N,N-Trimethyl-2-[(2-Methyl-1-Oxo-2-Propenyl )Oxy]-, Methyl Sulfate, Homopolymer), Quaternium-15 (Ethanaminium, N,N,N-Trimethyl-2-[(2-Methyl-1-Oxo-2-Propenyl)Oxy]-Chloride, Polymer with 2-Propenamide), Sodium Benzoate, Sodium Butylparaben, Sodium p-Chloro-m-Cresol, Sodium Dehydroacetate, Sodium Ethylparaben, Sodium Formate, Sodium Hydroxymethane Sulfonate, Sodium Hydroxymethylglycinate, Sodium Isobutylparaben, Sodium Isopropylparaben, Sodium Lauryl Diethylenediaminoglycinate, Sodium Methylparaben, Sodium Paraben, Sodium Phenolsulfonate, Sodium Phenoxide, Sodium o-Phenylphenate, Sodium Propionate, Sodium Propylparaben, Sodium Sorbate, Sorbic Acid, TEA-Sorbate (Triethanolamine Sorbate), Thianthol (Thianthrene, 2,7-dimethyl-), Triclocarban, Triclosan, and Undecylenoyl PEG-5 Paraben (ester of undecylenic acid and PEG-5 paraben).

At least one of such a non-formaldehyde-donating preservatives is added to a composition comprising at least one peptide copper complex, in particular, where the composition is aqueous, to thereto impart resistance to microbial attack and toxicity to microbes present therein. The use of more than one preservative may increase the efficacy thereof in this regard, owing to a synergistic effect. Accordingly, in an other embodiment of a disclosed preserved and chemically stable composition, the at least one non-formaldehyde-donating preservative is a paraben, a substituted paraben, chlorophenesin, phenoxyethanol, iodopropynyl butylcarbonate, triclosan, benzyl alcohol, benzoic acid, a benzoate, a substituted benzoate, a substituted paraben, or a salt thereof.

In view of the beneficial health and cosmetic applications of compositions comprising peptide copper complexes, as previously noted, the present invention is also directed to disclosed preserved and chemically stable compositions that are formulated for use as pharmaceutical and cosmetic products. Accordingly, in another embodiment of the present invention, a disclosed composition further comprises an inert and physiologically-acceptable carrier or diluent, where, in a related, more specific embodiment, the carrier or diluent is water, physiological saline, bacteriostatic saline, or a complex pharmaceutical or cosmetic formulation comprising a gel, cream, lotion, serum, milk, and the like. Such formulations would be known to one skilled in the art.

In another embodiment, a disclosed composition further comprises a sunscreen agent, a skin conditioning agent, a tanning agent, a skin protectant, an emollient, a humectant, or a mixture thereof, and in a yet further embodiment, a disclosed composition further comprises a fatty alcohol, a fatty acid, an organic base, an inorganic base, a wax ester, a steroid alcohol, a triglyceride ester, a phospholipid, a polyhydric alcohol ester, a fatty alcohol ether, a hydrophilic lanolin derivative, a hydrophilic beeswax derivative, a cocoa butter wax, a silicon oil, a pH balancer, a cellulose derivative, a hydrocarbon oil, or a mixture thereof.

The present invention, in another embodiment, is directed to a disclosed preserved and chemically stable composition that is formulated as an emulsion and topically applied to skin. In this embodiment, a disclosed composition further comprises an emulsifying agent, a surfactant, a thickening agent, an excipient, or a mixture thereof. Accordingly, the above-disclosed preserved and chemically stable compositions may be in the form of a liquid, lotion, cream, gel, emulsion, or microemulsion.

A discussion of, and examples of, physiologically-acceptable carriers and diluents, sunscreen agents, skin conditioning agents, skin protectants, emollients, humectants, surfactants, emulsifying agents, thickening agents and excipients may be found in, for example, U.S. Provisional Application Nos. 60/400,318; 60/393,563; 60/425,203 and 60/424,550; and in U.S. application Ser. Nos. 10/264,427; 10/264,363 and 10/264,392; all of which are incorporated herein by reference in their entireties.

Also, one skilled in the art will appreciate that the above-disclosed preserved and chemically stable compositions may comprise ingredients other than those listed above, such as, for example, an active drug substance.

In another embodiment of the present invention, the compositions of the present invention, adapted for topical application to the skin, may also contain at least one active cosmetic ingredient, in addition to the at least one peptide copper complex and non-formaldehyde donating preservative. Active cosmetic ingredients, as defined herein, are compounds that provide benefits to the skin and/or desirable properties to cosmetic formulations. Some examples of active ingredients are sunscreens and tanning agents, skin conditioning agents, skin protectants, emollients and humectants. Other active ingredients are defined herein are known to those in the art as cosmetic actives such as retinol, retinoids, various phytochemicals, various matrix metalloprotease inhibitors, and the like.

The present invention, in a further embodiment, is directed to a disclosed preserved and chemically stable composition comprising at least one peptide copper complex and at least one non-formaldehyde-donating preservative, and further comprising propylene glycol. The propylene glycol is used to dissolve the non-formaldehyde-donating preservative when the latter is present in an aqueous medium at a high concentration. One skilled in the art will appreciate that solvents, other than propylene glycol, may be used for this purpose.

In another embodiment, the at least one peptide copper complex of a disclosed composition is encapsulated in a liposome or microsponge adapted, as is well understood by one skilled in the art, to aid in the delivery of the peptide copper complex, or to enhance the stability of the composition. In yet another embodiment, the at least one peptide copper complex is formulated in an instrument adapted to deliver the peptide copper complex via iontophoresis or ultrasound, also, as is well understood by one skilled in the art.

The present invention, in a related aspect, is directed to medical devices that comprise a disclosed preserved and chemically stable composition. One non-limiting example of such a device is a sterile gauze pad, impregnated with a disclosed composition in the form of a gel for application to a wound.

In yet another aspect, the present invention is directed to a method for inhibiting microbial growth and/or reducing microbe populations in a composition, for example, an aqueous composition, comprising at least one peptide copper complex, while also substantially preserving the chemical stability of the peptide copper complex. More specifically, the method comprises incorporating a non-formaldehyde-donating preservative into the composition. As an example of such incorporation, a quantity of the preservative may be dissolved in an aqueous solution comprising the peptide copper complex.

The following examples, which illustrate the preparation, characterization, and utility of certain embodiments of the present invention, are provided for the purpose of illustration, not limitation. For all examples, concentrations are expressed as a percentage by weight of the solution.

EXAMPLE 1

An aqueous solution was prepared in isotonic saline containing the following additions:

0.1% peptide copper complex [Glycyl-L-Histidyl-L-Lysine Copper Complex]

0.2% methylparaben 0.02% propylparaben

The preservatives used are non-formaldehyde-donating preservatives. The solution was placed in a series of small sealed glass vials and stored at room temperature, at 40° C. and at 50° C. At various measured times, the amount of the peptide copper complex and of the preservatives was determined. The results of the assays are shown in Tables 4–6 below.

TABLE 4

Amounts when Stored at Room Temperature (mg/mL)

| Time (weeks) | Glycyl-L-Histidyl-L-Lysine: Copper(II) | Methylparaben | Propylparaben |
|---|---|---|---|
| 0 | 1.06 | 1.83 | 0.18 |
| 1 | 1.05 | 1.81 | 0.18 |
| 2 | 1.06 | 1.84 | 0.18 |
| 3 | 1.07 | 1.82 | 0.18 |
| 4 | 1.07 | 1.81 | 0.18 |
| 28 | 1.05 | 1.80 | 0.18 |

TABLE 5

Amounts when Stored at 40° C. (mg/mL)

| Time (weeks) | Glycyl-L-Histidyl-L-Lysine: Copper(II) | Methylparaben | Propylparaben |
|---|---|---|---|
| 0 | 1.06 | 1.83 | 0.18 |
| 1 | 1.04 | 1.79 | 0.18 |
| 2 | 1.07 | 1.80 | 0.18 |
| 3 | 1.06 | 1.77 | 0.18 |
| 4 | 1.06 | 1.75 | 0.18 |

TABLE 6

Amounts when Stored at 50° C. (mg/mL)

| Time (weeks) | Glycyl-L-Histidyl-L-Lysine: Copper(II) | Methylparaben | Propylparaben |
|---|---|---|---|
| 0 | 1.06 | 1.83 | 0.18 |
| 1 | 1.05 | 1.77 | 0.18 |
| 2 | 1.04 | 1.70 | 0.17 |
| 3 | 1.04 | 1.65 | 0.17 |
| 4 | 1.04 | 1.63 | 0.17 |

The solution was also adequately preserved, as shown by the results below. Specifically, the solution was tested for its ability to inhibit microbial growth. Testing was performed by standard methods as described in the current USP <51>. The microorganisms tested included *Canada ablicans* (*C. albicans*), *Aspergillus niger* (*A. niger*), *Escherichia coli* (*E. coli*), *Pseudomonas aeruginosa* (*P. aeruginosa*), and *Staphylcoccus aureus* (*S. aureus*). Testing of the samples gave the results shown in Table 7 below. As shown, the solution of peptide copper complex, with preservatives added, inhibited microbial growth and/or was toxic to microbial growth.

TABLE 7

Inhibition of Microbial Growth

|  | A. niger | C. albicans | E. coli | P. aeruginosa | S. aureus |
|---|---|---|---|---|---|
| Day 0 | 190,000 | 800,000 | 1,100,000 | 750,000 | 1,200,000 |
| Day 7 | <100 | 300 | <100 | <100 | <100 |
| Day 14 | <100 | <100 | <100 | <100 | <100 |
| Day 21 | <100 | <100 | <100 | <100 | <100 |
| Day 28 | <100 | <100 | <100 | <100 | <100 |

This example demonstrates the chemical stability of the peptide copper complex in the presence of a mixture of non-formaldehyde-donating preservatives that are paraben-type preservatives, where the latter effectively inhibit microbial growth.

EXAMPLE 2

A series of aqueous solutions were prepared containing the following additions.

Solution 2A 7.5% peptide copper complex [Glycyl-L-Histidyl-L-Lysine Copper(II)]

Solution 2B 7.5% peptide copper complex [Glycyl-L-Histidyl-L-Lysine Copper(II)]
  0.3% Diazolidinyl Urea (formaldehyde-donating)
  0.1% methylparaben
  0.03% propylparaben
  0.56% Propylene Glycol

Solution 2C 7.5% peptide copper complex [Glycyl-L-Histidyl-L-Lysine Copper(II)]
  0.3% Imidazolidinyl Urea (formaldehyde-donating)
  0.1% Methylparaben Sodium
  0.03% Propylparaben Sodium The solutions were placed in a series of small vials and stored at room temperature or at 40° C. At various measured times, the amount of peptide copper complex was determined in each sample. The results of the assays are shown in Table 8 below. Shown are the % changes in the amount of the peptide copper complex.

TABLE 8

% Change in Amount of Glycyl-L-Histidyl-L-Lysine:Copper(II) When Stored at Room Temperature (25° C.)

| Time (months) | Solution 2A | Solution 2B | Solution 2C |
|---|---|---|---|
| 0 | 0 | 0 | 0 |
| 1 | −0.14% | 3.0% | −2.95% |
| 2 | −0.11% | −2.29% | −0.42% |
| 3 | 1.24% | −1.00% | −1.83% |
| 6 | −0.14% | −1.71% | −3.09% |
| 12 | −0.55% | −5.57% | −2.67% |

The concentration of the peptide copper complex in solution 2A, stored without having a preservative contained therein, remained essentially unchanged after 12 months at room temperature. In contrast, for solutions 2B and 2C, each solution containing a formaldehyde-donating preservative (Diazolidinyl Urea or Imidazolidinyl Urea), there was significant breakdown of the peptide copper complex contained therein.

As Example 1 demonstrated that the paraben-type, non-formaldehyde-donating preservatives were compatible with the peptide copper complex with regard to the chemical stability thereof, the formaldehyde-donating preservatives used in this example were responsible for the above-demonstrated breakdown of the peptide copper complex.

More dramatic results were observed where solutions 2A, 2B and 2C were stored at 40° C., as shown in Table 9.

TABLE 9

% Change in Amount of Glycyl-L-Histidyl-L-Lysine:Copper(II) When Stored at Temperature of 40° C.

| Time (months) | Solution A | Solution B | Solution C |
|---|---|---|---|
| 0 | 0 | 0 | 0 |
| 1 | 0 | −2.14% | −7.02% |
| 2 | −0.55% | −5.86% | −6.74% |
| 3 | 0.82% | −5.71% | −5.62% |
| 6 | −1.65% | −9.57% | −12.22% |

The concentration of the peptide copper complex in solution 2A, stored without having a preservative contained therein, remained essentially unchanged after 6 months at 40° C., being reduced by less than 2%. In contrast, for both solutions 2B and 2C, each solution containing a formaldehyde-donating preservative (Diazolidinyl Urea or Imidazolidinyl Urea), there was considerable breakdown after 6 months of the peptide copper complex initially contained therein—about a 10% reduction thereof for solution B, and about a 12% reduction thereof for solution C.

EXAMPLE 3

Solutions of glycyl-L-histidyl-L-lysine:copper(II) were prepared at a concentration of 8% with and without the addition of a preservative or selected preservatives.

| Solution 3A | |
|---|---|
| Purified Water | q.s. 100% |
| Glycyl-L-Histidyl-L-Lysine:Copper(II) | 8% |
| Imidazolidinyl Urea | 0.3% |
| Methylparaben | 0.1% |
| Propylparaben | 0.03% |
| pH | 6.4 |
| Solution 3B | |
| Purified Water | q.s. 100% |
| Glycyl-L-Histidyl-L-Lysine:Copper(II) | 8% |
| Diazolidinyl Urea | 0.3% |
| Methylparaben | 0.11% |
| Propylparaben | 0.03% |
| Propylene Glycol | 0.56% |
| pH | 6.3 |
| Solution 3C | |
| Purified Water | q.s. 100% |
| Glycyl-L-Histidyl-L-Lysine:Copper(II) | 8% |
| pH | 6.5 |
| Solution 3D | |
| Purified Water | q.s. 100% |
| Glycyl-L-Histidyl-L-Lysine:Copper(II) | 8% |
| pH | 5.0 |

-continued

| Solution 3E | |
| --- | --- |
| Purified Water | q.s. 100% |
| Glycyl-L-Histidyl-L-Lysine:Copper(II) | 8% |
| Glycine | 1.6% |
| Diazolidinyl Urea | 0.3% |
| Methylparaben | 0.11% |
| Propylparaben | 0.03% |
| Propylene Glycol | 0.56% |
| pH | 6.4 |

After formulation, the solutions were filtered through 0.2 micron filters and tested for their ability to inhibit microbial growth. Testing was performed by standard methods as described in the current USP <51>. The microorganisms tested included Canada albicans (C. albicans), Aspergillus niger (A. niger), Escherichia coli (E. coli), Pseudomonas aeruginosa (P. aeruginosa), and Staphylcoccus aureus (S. aureus). Testing of the samples gave results set forth in Tables 10–14. In all cases, the aqueous solutions of peptide copper complex, with or without addition of preservatives, inhibited microbial growth or were toxic to microbes.

TABLE 10

INHIBITION OF MICROBIAL GROWTH BY SOLUTION 3A

| | A. niger | C. albicans | E. coli | P. aeruginosa | S. aureus |
| --- | --- | --- | --- | --- | --- |
| Day 0 | 170,000 | 490,000 | 600,000 | 440,000 | 500,000 |
| Day 14 | <100 | <100 | <100 | <100 | <100 |
| Day 28 | <100 | <100 | <100 | <100 | <100 |

TABLE 11

INHIBITION OF MICROBIAL GROWTH BY SOLUTION 3B

| | A. niger | C. albicans | E. coli | P. aeruginosa | S. aureus |
| --- | --- | --- | --- | --- | --- |
| Day 0 | 170,000 | 490,000 | 600,000 | 440,000 | 500,000 |
| Day 14 | <100 | <100 | <100 | <100 | <100 |
| Day 28 | <100 | <100 | <100 | <100 | <100 |

TABLE 12

INHIBITION OF MICROBIAL GROWTH BY SOLUTION 3C

| | A. niger | C. albicans | E. coli | P. aeruginosa | S. aureus |
| --- | --- | --- | --- | --- | --- |
| Day 0 | 170,000 | 490,000 | 600,000 | 440,000 | 500,000 |
| Day 14 | 57,000 | 58,000 | <100 | <100 | <100 |
| Day 28 | 57,000 | <100 | <100 | <100 | <100 |

TABLE 13

INHIBITION OF MICROBIAL GROWTH BY SOLUTION 3D

| | A. niger | C. albicans | E. coli | P. aeruginosa | S. aureus |
| --- | --- | --- | --- | --- | --- |
| Day 0 | 170,000 | 490,000 | 600,000 | 440,000 | 500,000 |
| Day 14 | <100 | 100,000 | <100 | <100 | <100 |
| Day 28 | <100 | 200 | <100 | <100 | <100 |

TABLE 14

INHIBITION OF MICROBIAL GROWTH BY SOLUTION 3E

| | A. niger | C. albicans | E. coli | P. aeruginosa | S. aureus |
| --- | --- | --- | --- | --- | --- |
| Day 0 | 170,000 | 490,000 | 600,000 | 440,000 | 500,000 |
| Day 14 | <100 | <100 | <100 | <100 | <100 |
| Day 28 | <100 | <100 | <100 | <100 | <100 |

EXAMPLE 4

Two cosmetic formulations were prepared containing a representative peptide copper complex, Glycyl-L-Histidyl-L-Lysine Copper, and either a formaldehyde donating preservative (Formulation 4A, diazolidinyl urea and paraben mixture) or a non-formaldehyde donating preservative mixture (Formulation 4B, phenoxyethanol, chlorphenesin). Both formulations were stored at 45° C. for 4 weeks and the percent of original peptide copper complex remaining was determined.

| Formulation 4A | Formulation 4B |
| --- | --- |
| Water | Water |
| Methyl Gluceth-20 | Methyl Gluceth-20 |
| PEG-8 | PEG-8 |
| Propylene Glycol | Propylene Glycol |
| PCA | PCA |
| Diisopropyl Dimer Dilinoleate | Diisopropyl Dimer Dilinoleate |
| Diisostearyl Dimer Dilinoleate | Diisostearyl Dimer Dilinoleate |
| Tocopherol | Tocopherol |
| Tocopheryl Linoleate | Tocopheryl Linoleate |
| Tocopheryl Acetate | Tocopheryl Acetate |
| Retinyl Palmitate | Retinyl Palmitate |
| Oryzanol | Oryzanol |
| Ubiquinone | Ubiquinone |
| Sodium Hyaluronate | Sodium Hyaluronate |
| Sodium Carboxymethyl Betaglucan | Sodium Carboxymethyl Betaglucan |
| Camellia Oleifera Leaf Extract | Camellia Oleifera Leaf Extract |
| Vitis Vinifera (Grape) Seed Extract | Vitis Vinifera (Grape) Seed Extract |
| Hydroxyethylcellulose | Hydroxyethylcellulose |
| Dimethicone Copolyol | Dimethicone Copolyol |
| Triethanolamine | Triethanolamine |
| PPG-26-Buteth-26 | PPG-26-Buteth-26 |
| PEG-40 Hydrogenated Castor Oil | PEG-40 Hydrogenated Castor Oil |
| Butylene Glycol | Butylene Glycol |
| | Glycerin |
| Diazolidinyl Urea (Formaldehyde donating) | Phenoxyethanol |
| Methylparaben | Chlorphenesin |
| Propylparaben | Methylparaben |
| | Benzoic Acid |

The formulation with the formaldehyde donating preservative (Formula 4A) lost 37% of the original peptide copper complex at 4 weeks, while the formulation with a non-formaldehyde donating preservative (Formulation 4B) lost only about 3% of the original peptide copper complex at 4 weeks.

The solutions were also adequately preserved, as shown by the results below. Specifically, the solutions were tested for their ability to inhibit microbial growth. Testing was performed by standard methods. The microorganisms tested included Bacterial Pool 1: *Escherichia coli, Staphylococcus aureus, Enterobacter cloacae & Proteus vulgaris*, Bacterial Pool 2: *Pseudomanas Aeruginosa, Pseudomanas cepacia, Pseudomanas fluorescens*, Fungal Pool: *Aspergillus niger & Candida albicans*

Testing of the samples gave the results shown in Tables 15 and 16 below.

TABLE 15

ANTIMICROBIAL EFFECTIVENESS OF FORMULATION 4A

| | Bacterial Pool 1<br>Escherichia coli<br>Staphylococcus aureus<br>Enterobacter cloacae<br>Proteus vulgaris | Bacterial Pool 2<br>Pseudomanas Aeruginosa<br>Pseudomanas cepacia<br>Pseudomanas fluorescens | Fungal Pool<br>Aspergillus niger<br>Candida albicans |
|---|---|---|---|
| Inoculum | $3.1 \times 10^6$ | $1.6 \times 10^6$ | $5.5 \times 10^5$ |
| Day 0 | $5.8 \times 10^4$ | $9.4 \times 10^3$ | $5.0 \times 10^4$ |
| Day 2 | <10 | <10 | <10 |
| Day 7 | <10 | <10 | <10 |
| Day 14 | <10 | <10 | <10 |
| Day 21 | <10 | <10 | <10 |
| Day 28 | <10 | <10 | <10 |

TABLE 16

ANTIMICROBIAL EFFECTIVENESS OF FORMULATION 4B

| | Bacterial Pool 1<br>Escherichia coli<br>Staphylococcus aureus<br>Enterobacter cloacae<br>Proteus vulgaris | Bacterial Pool 2<br>Pseudomanas Aeruginosa<br>Pseudomanas cepacia<br>Pseudomanas fluorescens | Fungal Pool<br>Aspergillus niger<br>Candida albicans |
|---|---|---|---|
| Inoculum | $3.9 \times 10^6$ | $2.3 \times 10^6$ | $4.9 \times 10^6$ |
| Day 0 | $1.3 \times 10^6$ | $4.2 \times 10^5$ | $5.6 \times 10^5$ |
| Day 2 | <10 | <10 | $1.7 \times 10^5$ |
| Day 7 | <10 | <10 | 210 |
| Day 14 | <10 | <10 | 170 |
| Day 21 | <10 | <10 | 20 |
| Day 28 | <10 | <10 | 10 |

As shown, the cosmetic formulations of peptide copper complex, with either non-formaldehyde donating or formaldehyde donating preservatives added, inhibited microbial growth and/or was toxic to microbial growth.

The above examples demonstrate that compositions comprising at least one peptide copper complex can be rendered resistant and/or toxic to microbial growth, as well as chemically stable, by the addition of a preservative selected to be a non-formaldehyde-donating preservative. As shown, the addition of a formaldehyde-donating preservative may impart resistance and/or toxicity to microbial growth; however, significant chemical breakdown of the peptide copper complex may follow.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A preserved and chemically stable composition comprising at least one peptide copper complex and a preservative, wherein the preservative consists essentially of at least one non-formaldehyde-donating preservative, and wherein the at least one non-formaldehyde-donating preservative is selected from the group consisting of ammonium benzoate, ammonium propionate, benzisothiazolinone, benzoic acid, benzotriazole, benzylparaben, 5-bromo-5-nitro-1,3-dioxane, 2-bromo-2-nitropropane-1,3-diol, butyl benzoate, calcium benzoate, calcium paraben, calcium propionate, calcium salicylate, calcium sorbate, chlorhexidine diacetate, chlorhexidine digluconate, chlorhexidine dihydrochloride, chloroacetamide, chlorobutanol, p-chloro-m-cresol, chlorophene, p-chlorophenol, chlorophenesin, chlorothymol, chloroxylenol, m-cresol, o-cresol, p-cresol, dehydroacetic acid, dibromopropamidine diisethionate, dimethyl oxazolidine, dithiomethylbenzamide, domiphen bromide, ethyl ferulate, ferulic acid, glyoxal, hexamidine, hexamidine diparaben, hexamidine paraben, 4-hydroxybenzoic acid, hydroxymethyl dioxoazabicyclooctane, iodopropynyl butylcarbamate, isodecylparaben, isopropyl cresols, isopropyl sorbate, lauryl diethylenediaminoglycine HCl, magnesium benzoate, magnesium propionate, MEA-benzoate, MEA o-phenylphenate, methyl-chloroisothiazolinone, methyl-dibromo methylisothiazolinone, octylisothiazolinone, panthenyl ethyl ether benzoate, phenethyl alcohol, phenol, phenoxyethylparaben, phenoxyisopropanol, phenyl benzoate, phenylparaben, o-phenylphenol, polymethoxy bicyclic oxazolidine, potassium benzoate, potassium butylparaben, potassium ethylparaben, potassium methylparaben, potassium paraben, potassium phenoxide, potassium o-phenylphenate, potassium propionate, potassium propylparaben, potassium sorbate, propionic acid, propyl benzoate, quaternium-8, quaternium-14, quaternium-15, sodium benzoate, sodium butylparaben, sodium p-chloro-m-cresol, sodium dehydroacetate, sodium ethylparaben, sodium formate, sodium hydroxymethane sulfonate, sodium hydroxymethylglycinate, sodium isobutylparaben, sodium isopropylparaben, sodium lauryl diethylenediaminoglycinate, sodium methylparaben, sodium paraben, sodium phenolsulfonate, sodium phenoxide, sodium o-phenylphenate, sodium propionate, sodium propylparaben, sodium sorbate, sorbic acid, triethanolamine sorbate, thianthol, triclocarban, triclosan, and undecylenoyl PEG-5paraben.

2. The composition of claim 1 wherein the at least one peptide copper complex is present at a concentration ranging from about 0.05% to about 25% by weight of the composition.

3. The composition of claim 1 wherein the at least one peptide copper complex is present at a concentration ranging from about 0.05% to about 2% by weight of the composition.

4. The composition of claim 1 wherein the at least one peptide copper complex is present at a concentration ranging from about 0.1% to about 0.5% by weight of the composition.

5. The composition of claim 1 wherein the molar ratio of peptide to copper in the at least one peptide copper complex ranges from about 1:1 to about 3:1.

6. The composition of claim 1 wherein the at least one peptide copper complex is glycyl-L-histidyl-L-lysine:copper(II).

7. The composition of claim 1 wherein the at least one peptide copper complex is L-alanyl-L-histidyl-L-lysine:copper(II).

8. The composition of claim 1 wherein the at least one peptide copper complex is L-valyl-L-histidyl-L-lysine:copper(II).

9. The composition of claim 1 wherein the at least one peptide copper complex is composed of a peptide or mixture of peptides formed by the hydrolysis of naturally occurring proteins, polypeptides, and larger peptides of either plant, microbial, or animal origin.

10. The composition of claim 1 wherein the composition is an aqueous solution having a pH adjusted to from about 4.5 to about 7.5.

11. The composition of claim 1 wherein the composition further comprises propylene glycol.

12. The composition of claim 1 wherein the at least one peptide copper complex is encapsulated in a liposome or microsponge adapted to aid in the delivery of the peptide copper complex, or to enhance the stability of the composition.

13. The composition of claim 1 wherein the at least one peptide copper complex is formulated in an instrument adapted to deliver the peptide copper complex via iontophoresis or ultrasound.

14. The composition of claim 1, further comprising an inert and physiologically-acceptable carrier or diluent.

15. The composition of claim 14 wherein the inert and physiologically-acceptable carrier or diluent is water, physiological saline, bacteriostatic saline, a petrolatum based cream, a pharmaceutically acceptable gel, a short chain alcohol, or a short chain glycol.

16. The composition of claim 1 wherein the composition is a complex pharmaceutical or cosmetic formulation comprising a gel, cream, lotion, serum, or milk.

17. The composition of claim 1, further comprising a sunscreen agent, a skin conditioning agent, a tanning agent, a skin protectant, an emollient, or a humectant.

18. The composition of claim 1, further comprising a fatty alcohol, a fatty acid, an organic base, an inorganic base, a preserving agent, a wax ester, a steroid alcohol, a triglyceride ester, a phospholipid, a polyhydric alcohol ester, a fatty alcohol ether, a hydrophilic lanolin derivative, a hydrophilic beeswax derivative, a cocoa butter wax, a silicon oil, a pH balancer, a cellulose derivative, a hydrocarbon oil, or a mixture thereof.

19. The composition of claim 1, further comprising an emulsifying agent, a surfactant, a thickening agent, an excipient, or a mixture thereof.

20. The composition of claim 1 wherein the composition is in the form of a liquid, lotion, cream, gel, emulsion, or microemulsion.

21. The composition of claim 1, further comprising an active drug substance.

22. The composition of claim 1, further comprising an active cosmetic substance.

23. The composition of claim 1, further comprising an active cosmetic substance where the active cosmetic substance is retinol, retinoic acid, or derivatives thereof.

24. The composition of claim 1, further comprising an active cosmetic substance where the active cosmetic substance is a phytochemical.

25. A medical device comprising the composition of claim 1.

26. A method for inhibiting microbial growth or reducing microbe populations in a composition comprising at least one peptide copper complex, while also substantially preserving the chemical stability of the at least one peptide copper complex, wherein the method comprises incorporating a preservative into the composition, wherein the preservative consists essentially of at least one non-formaldehyde-donating preservative, and wherein the at least one non-formaldehyde-donating preservative is selected from the group consisting of ammonium benzoate, ammonium propionate, benzisothiazolinone, benzoic acid, benzotriazole, benzylparaben, 5-bromo-5-nitro-1,3-dioxane, 2-bromo-2-nitropropane-1,3-diol, butyl benzoate, calcium benzoate, calcium paraben, calcium propionate, calcium salicylate, calcium sorbate, chlorhexidine diacetate, chlorhexidine digluconate, chlorhexidine dihydrochloride, chloroacetamide, chlorobutanol, p-chloro-m-cresol, chlorophene, p-chlorophenol, chlorophenesin, chlorothymol, chloroxylenol, m-cresol, o-cresol, p-cresol, dehydroacetic acid, dibromopropamidine diisethionate, dimethyl oxazolidine, dithiomethylbenzamide, domiphen bromide, ethyl ferulate, ferulic acid, glyoxal, hexamidine, hexamidine diparaben, hexamidine paraben, 4-hydroxybenzoic acid, hydroxymethyl dioxoazabicyclooctane, iodopropynyl butylcarbamate, isodecylparaben, isopropyl cresols, isopropyl sorbate, lauryl diethylenediaminoglycine HCl, magnesium benzoate, magnesium propionate, MEA-benzoate, MEA o-phenylphenate, methyl-chloroisothiazolinone, methyl-dibromo methylisothiazolinone, octylisothiazolinone, panthenyl ethyl ether benzoate, phenethyl alcohol, phenol, phenoxyethylparaben, phenoxyisopropanol, phenyl benzoate, phenylparaben, o-phenylphenol, polymethoxy bicyclic oxazolidine, potassium benzoate, potassium butylparaben, potassium ethylparaben, potassium methylparaben, potassium paraben, potassium phenoxide, potassium o-phenylphenate, potassium propionate, potassium propylparaben, potassium sorbate, propionic acid, propyl benzoate, quaternium-8, quaternium-14, quaternium-15, sodium benzoate, sodium butylparaben, sodium p-chloro-m-cresol, sodium dehydroacetate, sodium ethylparaben, sodium formate, sodium hydroxymethane sulfonate, sodium hydroxymethylglycinate, sodium isobutylparaben, sodium isopropylparaben, sodium lauryl diethylenediaminoglycinate, sodium methylparaben, sodium paraben, sodium phenolsulfonate, sodium phenoxide, sodium o-phenylphenate, sodium propionate, sodium propylparaben, sodium sorbate, sorbic acid, triethanolamine sorbate, thianthol, triclocarban, triclosan, and undecylenoyl PEG-5 paraben.

27. A method for treating aging skin comprising contacting the skin with an effective amount of a composition of claim 1.

28. A method for treating wounds comprising contacting the wound with an effective amount a composition of claim 1.

29. A method for treating hyperpigmentation of skin comprising contacting the skin with an effective amount a composition of claim 1.

30. A method for cosmetic treatment of skin, comprising contacting skin with an effective amount of the composition of claim 1.

31. The method of claim 30 wherein the cosmetic treatment of skin is smoothening the skin, reducing hyperpigmentation of the skin, reducing wrinkles in the skin, reducing evidence of photodamage of the skin, or reducing the signs of aging in the skin.

* * * * *